United States Patent [19]

Martin

[11] Patent Number: 5,174,508

[45] Date of Patent: Dec. 29, 1992

[54] TABLET EXTRACTION AND ANALYSIS SYSTEM AND METHOD

[75] Inventor: Arthur L. Martin, Sherborn, Mass.

[73] Assignee: Source For Automation, Inc., Mass.

[21] Appl. No.: 745,946

[22] Filed: Aug. 16, 1991

[51] Int. Cl.$^5$ ............................................. B02C 23/36
[52] U.S. Cl. ................................. 241/21; 241/46.11; 241/DIG. 27
[58] Field of Search .................. 241/DIG. 27, 46.08, 241/46.11, 21

[56] References Cited

U.S. PATENT DOCUMENTS

| | | | |
|---|---|---|---|
| 1,541,115 | 6/1925 | China | 241/21 X |
| 2,318,911 | 4/1941 | Zweber et al. | |
| 2,461,720 | 2/1949 | Cawood et al. | 241/46.11 X |
| 2,602,596 | 4/1951 | Jones et al. | |
| 2,840,357 | 6/1958 | Nauta | |
| 2,892,595 | 6/1959 | Tupper | 241/DIG. 27 X |
| 2,903,198 | 9/1959 | Asplin | |
| 2,911,099 | 11/1959 | Schade | 241/46.08 X |
| 2,963,281 | 12/1960 | Reiffen | 241/46.11 X |
| 3,773,468 | 11/1973 | Hubbard et al. | 241/DIG. 27 X |
| 3,865,551 | 2/1975 | Saiki et al. | 241/DIG. 27 X |
| 3,894,694 | 7/1975 | Rothman | 241/46.11 |
| 4,307,846 | 12/1981 | Spelsberg | |
| 4,366,930 | 1/1983 | Trombetti, Jr. | |
| 4,715,545 | 12/1987 | Hanifl et al. | |
| 4,900,683 | 2/1990 | Metzger et al. | |

FOREIGN PATENT DOCUMENTS 621376 8/1978 U.S.S.R. .................... 241/DIG. 27

*Primary Examiner*—Mark Rosenbaum
*Assistant Examiner*—Frances Chin
*Attorney, Agent, or Firm*—Cesari and McKenna

[57] ABSTRACT

A tablet extractor includes a housing which defines a cylindrical chamber having a bottom wall and a side wall. A relief is formed in a sector of the chamber side wall which creates a relatively sharp knife edge. An impeller rotatably mounted in the housing includes a rigid finger which extends along the chamber, that finger having a leading face which extends generally radially and a radially outer surface which follows closely the unrelieved portions of the chamber side wall. There is an opening in the bottom wall of the chamber and a second opening in the chamber side wall. When the impeller is rotated so that the finger rotates toward the knife edge, the extractor can recirculate liquid and a tablet and parts thereof entrained in the liquid through the chamber for mixing and can position the tablet while in the chamber for impaction against the knife edge to pulverize the tablet. A complete automated extraction and analysis workstation incorporating the tablet extractor is also disclosed.

18 Claims, 3 Drawing Sheets

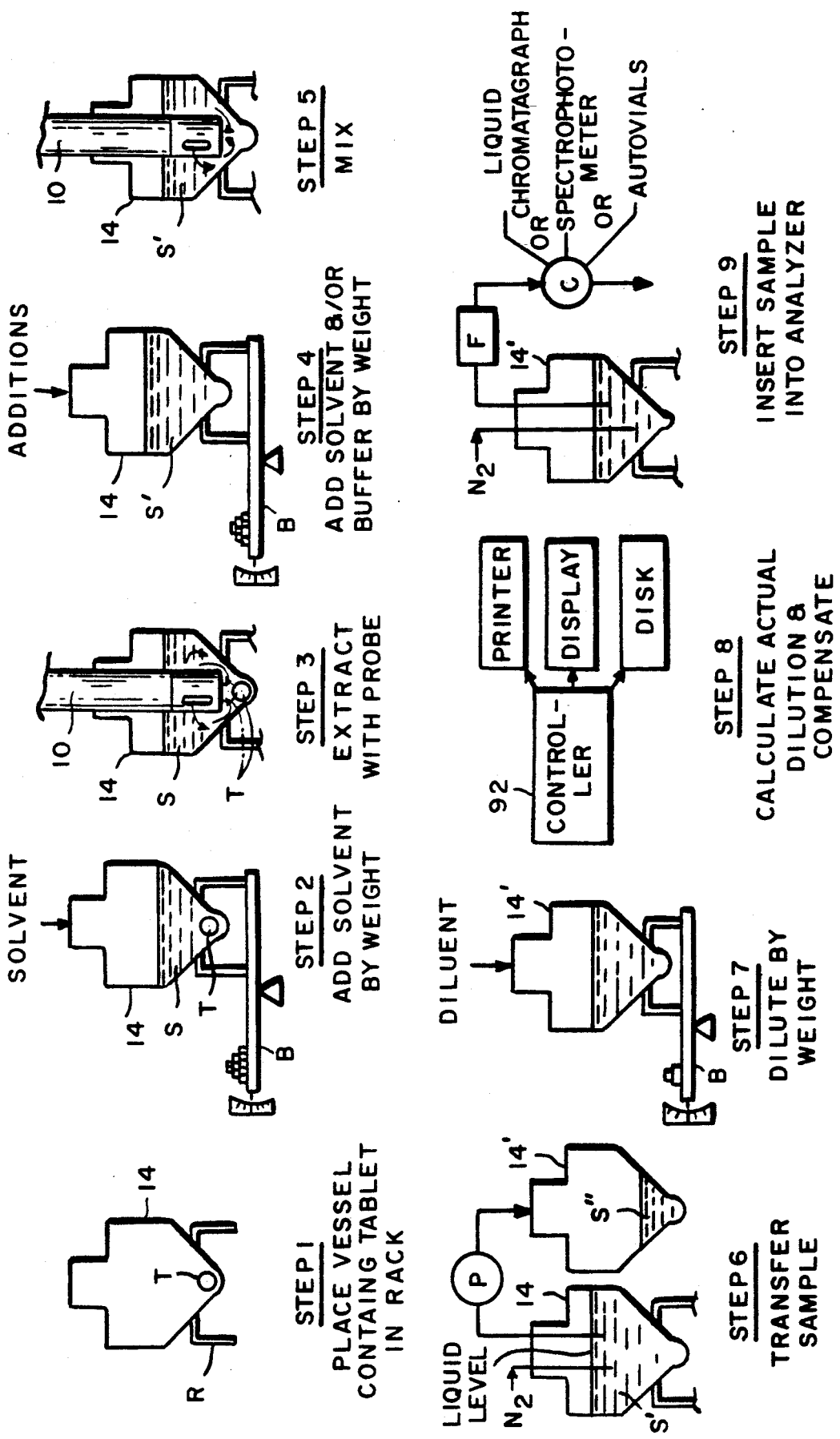

TABLET EXTRACTION AND ANALYSIS SYSTEM AND METHOD

This invention relates to tablet extraction and analysis. It relates especially to an improved tablet extractor for extracting the active ingredients of tablets.

BACKGROUND OF THE INVENTION

Drugs in the form of solid dosage tablets are often analyzed in pharmaceutical laboratories for their total content as well as for the uniformity of content. This data is used by pharmaceutical companies for quality control and other purposes. Traditionally, a tablet is prepared for analysis manually in a labor intensive procedure that is slow and can result in preparation errors. First, the tablet is placed in a volumetric flask. Solvent is then added and the flask is placed on a mechanical shaker or sonicator. This manual method is not only time consuming, but also prone to errors. It also generally requires the use of considerable amounts of solvents in order to fully dissolve the active ingredients of the tablet. Some of the solvents are dangerous and thus present a hazard to the chemist performing the analysis.

Some tablets are very hard and, therefore, difficult to dissolve. These tablets must be pulverized either manually, using a mortar and pestle, or mechanically, using various known pulverizing apparatus which either emulate a mortar and pestle by grinding the tablet between two relatively moving surfaces or mimic the crushing action of a hammer and/or, in the case of wet grinding, the shearing action of a homogenizer or blender. All such mechanical pulverizers and blenders are an improvement over the mortar and pestle as far as reducing the time it takes to get the active ingredients of most tablets into solution. However, they are still unable to process efficiently the harder tablets such as certain time release tablets that are in wide use at the present time. The extraction of these tablets is still done manually for the most part, or if done mechanically, it takes a relatively long time to release the active ingredients of those tablets into solution. Resultantly, it is difficult to provide a fully automated system for completely and reliably extracting and accurately analyzing the contents of such tablets. As a consequence, in many cases, it takes an inordinately long time to obtain the results of a particular assay and, even then, the results may be compromized by human error while performing the extraction.

SUMMARY OF THE INVENTION

The present invention aims to provide an improved tablet extractor.

A further object of the invention is to provide a tablet extractor which requires a minimum amount of solvent for the extraction.

Still another object of the invention is to provide an extractor of this type which can completely extract even very hard tablets.

Another object of the invention is to provide a tablet extractor which can release the active ingredients of even the hardest tablets into solution in seconds to a few minutes.

A further object of the invention is to provide a tablet extractor which can be incorporated into a fully automated tablet extraction and analysis system.

Another object of the invention is to provide a method of extracting tablets which produces one or more of the above advantages.

Other objects will, in part, be obvious and will, in part, appear hereinafter.

The invention accordingly comprises the features of construction, combination of elements and arrangement of parts and the sequence of steps which will be exemplified in the following detailed description, and the scope of the invention will be indicated in the claims.

Briefly, my tablet extractor is designed to be situated as a module in an automated extraction and analysis workstation. It is designed as a probe which can be inserted into an open top vessel containing a sample tablet and a suitable solvent. The extractor comprises an elongated tubular housing having a chamber at its lower end with a bottom opening. Extending along the housing is a rotary shaft with a impeller at its lower end located within the housing chamber. The shaft and impeller may be rotated relative to the housing at a high speed by a suitable electric motor.

The impeller includes a depending finger which extends down to the bottom of the housing chamber and which "wipes" the side wall of the chamber as the impeller is rotated. The leading surface of that finger is inwardly curved or dished so that when a tablet is introduced into the chamber, the finger captures the tablet and circulates it around the chamber adjacent to the chamber wall. A side opening in the housing side wall extends into the chamber. Also, the edge of the side opening facing the leading surface of the impeller finger is bevelled to form a vertical knife edge. Furthermore, the chamber wall is relieved adjacent to the opposite edge of that slot so that it lies radially outboard of the knife edge. Resultantly, when the tablet is advanced to that relieved sector of the chamber wall, it is positioned directly opposite the knife edge so that it will be smashed against that edge by the rotating impeller and be broken up and pulverized.

In use, after the extractor is inserted down into the vessel containing the tablet and solvent, the extractor's motor is turned on to rotate the impeller. The extractor functions as a combination pump and pulverizer which sucks up and digests the tablet. For this, the rapidly spinning impeller recirculates the solvent liquid through the extractor chamber by drawing it through the bottom opening in the housing and expelling it through the side opening therein. This creates a vortex in the solvent below the extractor which captures the tablet and draws the tablet up into the extractor chamber where it encounters the rapidly spinning impeller finger.

As noted above, the impeller finger captures the tablet and smashes it forcefully against the knife edge upon each revolution of the impeller. This process breaks up the tablet into smaller pieces which are, in turn, impacted against the knife edge. Those pieces that are small enough may be expelled out through the side opening and reintroduced into the chamber through the bottom opening by the recirculating liquid solvent. Thus, the tablet pieces and particles are subjected to an aggressive mixing action in the circulating solvent and, while in the extractor chamber, are spun around and subjected to the slicing/cutting action of the knife edge therein. Resultantly, even a very hard tablet is extracted completely in a minimum amount of time.

The pumping action of the extractor, in addition to assisting in the digestion and breaking up of the tablet, drives the liquid solvent along the walls of the vessel so that the liquid sweeps the tablet particles from those walls and recirculates them through the extractor so that the tablet contents are thoroughly dissolved in the solvent assuring a complete extraction of the entire tablet.

While the extractor may be operated continuously until the extraction is completed, most preferably it is operated in an intermittent mode with the impeller being alternately rotated at high speed and stopped. This intermittent operation tends to hasten the dissolution of the tablet and minimizes the volume of solvent required to effect the extraction. Usually the tablet can be fully extracted in a single operation. However, if necessary, after an initial extraction, additional solvents and buffers can be added to the vessel containing the tablet and by thoroughly mixed by another pass through the extractor. Following completion of the extraction, the extractor may be operated while probing into a solvent in a cleaning reservoir to eliminate carry-over to the next sample to be extracted.

My extractor preferably constitutes one module in a complete system for extracting and analyzing tablet samples. As will be described in detail later, the system delivers diluting solvents on a gravimetric, rather than a volumetric basis, assuring a very accurate assay with a deviation far below the industry standard.

BRIEF DESCRIPTION OF THE DRAWINGS

For a fuller understanding of the nature and objects of the invention, reference should be made to the following detailed description taken in conjunction with the accompanying drawings, in which:

FIG. 5 is a diagrammatic view showing a tablet extraction and analysis system and method incorporating the invention.

DESCRIPTION OF THE PREFERRED EMBODIMENT

Figure 1:
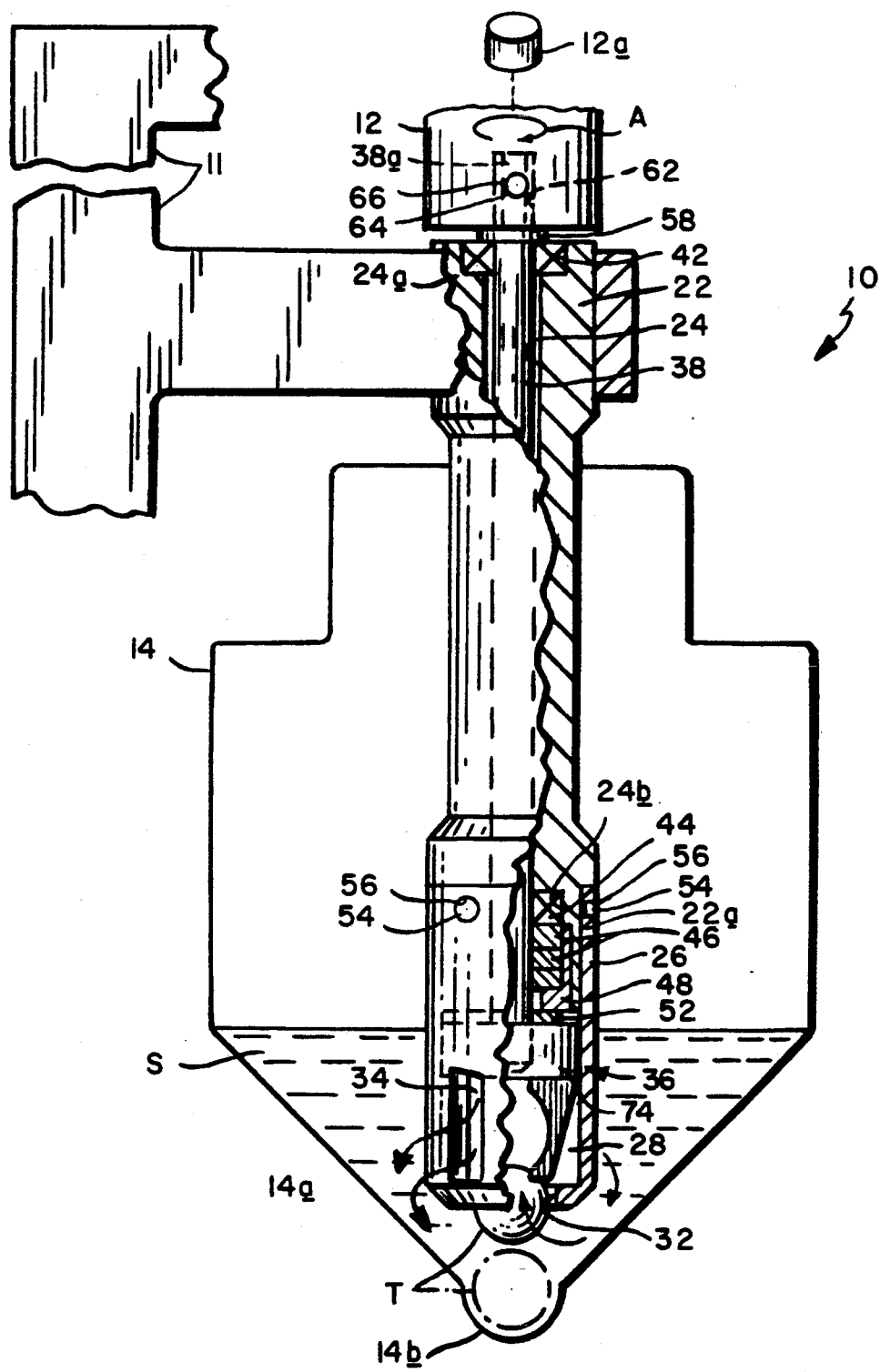
FIG. 1 is an elevational view with parts broken away showing a tablet extractor incorporating our invention.

Referring to FIG. 1 of the drawing, my extractor, shown generally at 10, is supported by a support block or bracket 11 so that the extractor projects down probe-like into the open top of a suitable vessel 14. When the extractor is in use, vessel 14 contains a sample tablet T and an appropriate solvent S for releasing the active ingredients of that tablet. Vessel 14 may be, for example, a readily available graduated conical tube having a volume in the order of 150 ml. Tablet T tends to gravitate to the very bottom region 14b of vessel 14 due to its conical bottom wall 14a. The tablet may be of any size but is usually less than 12 mm in diameter and may be virtually of any composition. The nature of the extraction solvent S depends upon the composition of the tablet to be extracted and is present in a volume sufficient to carry out the extraction process which volume is usually between 30 and 50 mls.

Still referring to FIG. 1, extractor 10 comprises a relatively long tubular housing 22 engaged by the support bracket 11 and having an axial passage 24 which extends the entire length of the housing. A lower end segment 22a of housing 22 has a reduced outer diameter and a generally cylindrical end cap 26 is telescoped onto that segment so as to form a cylindrical chamber 28 just below housing 22. In the illustrated extractor embodiment, chamber 28 is in the order of one inch in diameter and one inch high.

The bottom wall of end cap 26 is provided with a relatively large diameter opening 32 and a vertically oriented slot 34 is present in the end cap side wall, opening 32 and slot 34 both opening into chamber 28.

Positioned in chamber 28 is an impeller shown generally at 36. The impeller is mounted to the lower end of a long shaft 38 which extends up through passage 24 in housing 22, with the upper end of the shaft projecting from the upper end of the housing as shown in FIG. 1. The upper end of housing passage 24 is counterbored at 24a to receive a bearing unit 42 which encircles shaft 38 near its upper end. In a similar fashion, the lower end of passage 24 is counterbored at 24b to seat a second similar bearing unit 44 which encircles shaft 38 near its lower end. Packing rings 46 surround shaft 22 below bearing unit 44. These packing rings are captured by a collet 48 seated in a radial enlargement of counterbore 24b, the collet being held in place by a washer 52 encircling shaft 22 just above impeller 36.

The bearing unit 44, packing rings 46, collet 48, washer 52 and impeller 36 are installed in housing 22 prior to attaching the end cap 26 to the housing. Once those components are in place, the end cap may be telescoped onto the lower end of housing 22 and retained in place by suitable means such as set screws 54 threaded into holes 56 in the side wall of end cap 26 near the upper end thereof.

A locking ring 58 is engaged around shaft 38 just above housing 22 to fix the axial position of the shaft. Preferably, a flat 38a is provided on the projecting upper end segment of shaft 38 and that segment is keyed into an axial passage 62 in a shaft 12 of a high speed electric motor 12a also supported by bracket 11. Shaft 38 may be fastened in place by any suitable means such as a set screw 64 threaded into an opening 66 in the side of shaft 12 so as to engage flat 38a. The illustrated motor shaft 12 rotates in the clockwise direction indicated by the arrow A at a high speed, e.g. 7-10,000 rpm which assures an effective pumping/pulverizing action by the extractor.

Figure 2:
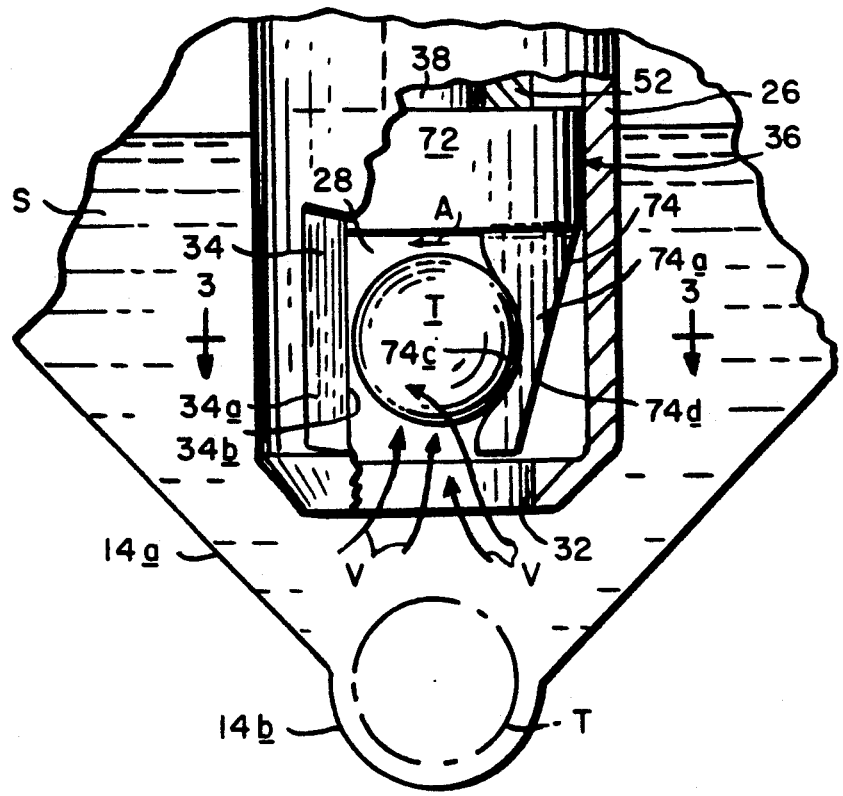
FIG. 2 is a similar view on a much larger scale showing parts of the FIG. 1 extractor in greater detail.
Figures 3, 4:
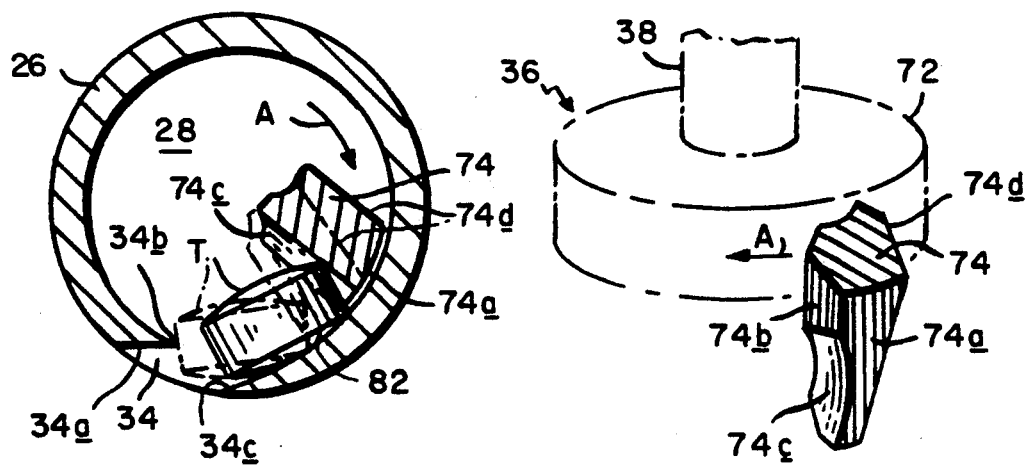
FIG. 3 is a sectional view taken along line 3—3 of FIG. 2.
FIG. 4 is a fragmentary isometric view showing a part of the extractor in greater detail.

Referring now to FIGS. 2 to 4, impeller 36 includes a discoid base 72 mounted to the lower end of shaft 38. Extending down from base 72 at the outer edge thereof is a specially profiled finger 74 which extends from the base almost to the bottom of chamber 28, e.g. about 5/8 inch, which is about the same a the length of side slot 34.

Finger 74 has a radially outer surface 74a which hugs the chamber 28 side wall and whose curvature matches that of the side wall. Finger 74 also has a leading face 74b which extends generally radially from surface 74a toward shaft 38. The leading face 74b is provided at its lower end with a vertically oriented concavity 74c whose curvature is the same as or less pronounced than that of tablet T so that when the tablet T is oriented on its side in chamber 28 as shown in FIG. 2 and the impeller 36 is rotated in the direction of arrow A, the tablet will be captured in the concavity 74c. The trailing surface 74d of finger 74 is tapered at an angle about 20° relative to the vertical direction as shown in FIG. 2 to reduce the weight of the finger.

As best seen in FIGS. 2 and 3, the side slot 34 and the wall of chamber 28 are specially shaped to cooperate with the impeller finger 74 to pump liquid through chamber 28 and to digest and break up tablet T in a minimum amount of time. More particularly, the edge of slot 34 toward which the tablet T is advanced when the impeller is rotating clockwise is provided with an outer bevel 34a to form a relatively sharp knife edge 34b right at the outer boundary of chamber 28. Also, the side wall of chamber 28 is not perfectly cylindrical throughout. Rather, a sector of the inner wall of end cap 26 adjacent to the opposite edge 34c of slot 34 is relieved where it opposes the impeller finger 74. This relief, shown at 82 in FIG. 3, may be very modest, e.g. 0.020 to 0.040 inch, to accomplish its purpose which is to promote the pumping action of the extractor and to assist positioning the tablet T so that when the tablet T is spun around chamber 28 by the rotating impeller finger 74, the tablet will be oriented edge-on to the knife edge 34b as shown in FIG. 3.

During the operation of extractor 10, container 14 containing a sample tablet T and a suitable solvent S is positioned under the extractor 10 s that the extractor extends down almost to the bottom of vessel 14 as shown in FIGS. 1 and 2. Preferably, the vessel contains.. sufficient solvent so that the solvent level extends above the extractor side slot 34. Then, the impeller 36 is rotated at high speed by the motor shaft 12 in the direction of arrow A. Resultantly, the finger 74 sweeps out a toroidal envelope whose outer boundary extends just inboard of slot 34 and knife edge 34b. However, as noted above, that boundary is spaced from the relieved sector 82 of the housing side wall.

The rotating impeller 36 produces a pumping action which sucks solvent S into chamber 28 through the bottom opening 32 and whirls the solvent around in chamber 28 and expels the solvent from the chamber through side slot 34. This pumping action creates a vortex V in the volume of solvent below the extractor which pulls the sample tablet T from the bottom 14b of the vessel up into the chamber 28 through opening 32 as shown in solid lines in FIG. 1. As the tablet and solvent swirl around in chamber 28, centrifugal force causes the tablet to orient itself so that one of its faces hugs the chamber wall so that the tablet is in position to be engaged and captured by the concave segment 74c of the impeller finger 74 as shown in FIGS. 2 and 3.

When the impeller finger 74 pushes the tablet to the relieved sector 82 of the chamber 28 wall, the tablet is usually positioned so that it is edge-on to the knife edge 32b of slot 34 as shown in phantom in FIG. 3. Resultantly, the edge of tablet T is driven by impeller 36 extremely forcefully against knife edge 34b which cuts into the tablet, breaking it into smaller pieces. Some of these pieces, particularly if they are relatively large, may be spun around chamber 28 many times by the impeller and be broken up into smaller and smaller pieces by repeatedly impacting against the knife edge. Smaller pieces of the tablet may be spewed out through side slot 34 and subjected to the dissolving and mixing action of the solvent vortex V as they are repeatedly sucked up into chamber 28 through bottom opening 32 and swirled around the chamber and expelled through the side slot. This pumping/pulverizing action is repeated again and again until the tablet is fully digested by the extractor and dissolved in the solvent S. The softer sample tablets may be extracted completely in a few seconds; the harder time-release types of tablets may require processing for a couple of minutes to be brought completely into solution.

In addition to accelerating the extraction process, the recirculating solvent in the vortex V constantly scours the walls of vessel 14 that no tablet particles can remain there which are not brought into solution. This ensures that each sample tablet is completely extracted so that the assay performed on that tablet will be accurate.

After completion of the extraction,.the container 14 is removed from the extractor, following which the extractor may be washed by raising a wash reservoir containing a wash solvent up to the extractor and operating the extractor so that the washing liquid is recirculated through the extractor. This will clean all of the interior and exterior surfaces of the extractor to assure that there is no carryover when the extractor 10 is used to extract the next sample tablet.

As noted previously, extractor 10 may be present as one module of a multimode automated workstation which may extract and analyze a succession of sample tablets. The various stages in such a system are shown diagrammatically in FIG. 5. The various steps in the process may be carried out at modules integrated into a complete tablet extraction and analysis workstation.

First, in Step 1, the sample tablet T is delivered to the system in a vessel 14 and placed in a rack R. Next, at a dispensing station for Step 2, a suitable solvent S is dispensed into the vessel. The solvent is one which will extract the active ingredients of the particular tablet. For example, if the tablet T is prednisone, the solvent S may be methanol. The solvent is added while the vessel is on a balance B built into the workstation and the amount of the solvent added is determined gravimetrically, rather than volumetrically. In other words, the solvent is introduced into the vessel using a nonmetered peristaltic pump (not shown) and the pump is controlled by a controller 92 to dispense a selected weight of solvent into the vessel as will be described in more detail shortly.

In Step 3, the vessel 14 is moved to the extraction station and positioned under extractor 10. The vessel is then raised so that the extractor projects almost to the bottom of the vessel as shown. The extractor may be operated to rotate impeller 36 either continuously or intermittently depending upon the hardness of the sample tablet being extracted. In general, as noted above, extraction by a series of pulses and pauses of the impeller enhances the extraction process and brings the active ingredients of the tablet into solution in a minimum amount of time.

After the tablet is fully extracted, the vessel 14 is removed from the extractor 10 and may be returned to the dispensing station where, in Step 4, while the vessel remains on a balance, more solvents and/or buffers relating to the particular assay may be added to the vessel. As before, these additional liquids are added according to weight rather than volume. After the introduction of these liquids, the vessel may be returned to the extractor station 10 where, in Step 5 of the process, the contents S' of the container may be subjected to the mixing action of the extractor 10.

In Step 6 of the process, a selected volume of the sample S' may be transferred from vessel 14 to a dilution vessel or tube 14' using a peristaltic pump P controlled in the same manner as described above.

Next, in Step 7 of the process, the vessel 14, may be placed at the dispensing station where the smaller sample S" in vessel 14, may be diluted with a suitable diluent. This step is also done gravimetrically while the vessel 14' is on a balance. Again at this stage, nitrogen gas may be introduced into the container for mixing purposes.

The balance B provides an output to the system controller 92 which, in Step 8, takes all of the gravimetrically dispensed volumes added to the sample at steps 2, 4, 6 and 7 of the process and determines the actual dilution as compared to the desired or targeted one.

More particularly, in accordance with my method, the dilution is made in three stages. In the initial stage, an initial volume is added to the sample. The addition can be made in one or more parts from different pumps, e.g., a selected amount of solvent $A_1$ may be added in process Step 2 and a selected amount of solvent $A_2$ may be added in process Step 4. In the second or transfer stage, a transfer is made from the initial volume in vessel 14 to the dilution vessel 14' in Step 6. This dilution is done in one shot. In the third or final stage, a final dilution is made at Step 7 of the process. Like the initial dilution, this may consist of more than one part, i.e. a dilution by more than one diluent.

The following variables are used to track the various steps in the dilution process:

TARGET VOLUME (TARVOL) is used to compute the volume to be dispensed from each pump based on the actual volume dispensed from previous pumps in the same stage. That is, each time a pump is used in a stage, the volume to be pumped by that pump is corrected by the volume actually dispensed from the previous pump in the same stage.

TARGET SUM (TARSUM) is used to compute and store the cumulative target volume that will be used in the formula used by the controller to determine the correction factors.

FINAL WEIGHT (FINWEIGHT) is TARGET VOLUME times diluent density; it is the weight variable used to control the pump.

ACTUAL VOLUME (ACTVOL) is the volume actually pumped during a particular pumping routine.

ACTUAL SUM (ACTSUM) is used to compute the cumulative volume dispensed during each of the three stages.

Assume, for example, that, in the initial stage, it is desired to add to a sample 50 cc of a solvent $A_1$ having a density of 0.987 and then 25 cc of a second solvent $A_2$ having a density of 0.871.

Part 1

TARSUM A = 50
TARVOL A = 50
FINWEIGHT = 50 × 0.987 = 49.4
TELL PUMP TO PUMP
ACTVOL A = 49.3
ACTSUM A = 49.3 (i.e., it is 0.7 less than the TARSUM)

Part 2

TARSUM A = 50 + 25 = 75
TARVOL A = 0.7 + 25 = 25.7
FINWEIGHT = 25.7 × 0.871 = 22.4
TELL PUMP TO PUMP
ACTVOL A = 25.9
ACTSUM A = 75.2 = TOTAL INITIAL DILUTION

Assume that in the transfer stage, 5 cc of solvent B having a density of 1 is targeted:

TARSUM B = 5
TARVOL B = 5
FINWEIGHT = 5 × 1 = 5
TELL PUMP TO PUMP
ACTVOL B = 4.9
ACTSUM B = 4.9 = FINAL TRANSFER DILUTION

Assume in the final stage that 30 cc of solvent $C_1$ having a specific gravity of 0.987 is targeted, followed by 15 cc of solvent $C_1$ having a specific gravity of 0.871.

Part 1

TARSUM C = 30
TARVOL C = 30
FINWEIGHT = 30 × 0.987 = 29.6
TELL PUMP TO PUMP
ACTVOL C = 29.5
ACTSUM C = 29.5

Part 2

TARSUM C = 30 + 15 = 45

At this point, the controller takes all of the gravimetrically dispensed volumes added above and computes the total actual dilution as follows:

TARGET DILUTION (TARDIL) = TARSUM A ×

$$\frac{(TARSUM\ B + TARSUM\ C)}{TARSUM\ B} = 75 \times \frac{(5 + 45)}{5} = 750$$

$$TARVOL\ C = TARDIL \times \frac{ACTSUM\ B}{ACTSUM\ A} - ACTSUM\ C -$$

$$ACTSUM\ B = 750 \times \frac{4.9}{75.2} - 29.5 - 4.9 = 14.47$$

FINWEIGHT = 14.47 × .871 = 12.6
TELL PUMP TO PUMP
ACTVOL C = 14.1
ACTSUM C = 43.6

TOTAL ACTUAL DILUTION = ACTSUM A ×

$$\frac{(ACTSUM\ C + ACTSUM\ B)}{ACTSUM\ B} =$$

$$75.2 \times \left(\frac{43.6 + 4.9}{4.9}\right) = 744.33$$

Thus in the above example, the particular assay called for a 750 cc dilution, but the actual dilution was only 744.33 cc, as determined by the above algorithm.

Data relating to the particular assay may be displayed to the chemist on a display associated with the controller and also may be printed and/or recorded on disk, as shown in FIG. 5.

Finally, in Step 9 of the process, while being mixed gently by a nitrogen gas purge, the sample in vessel 14' may be injected automatically into a conventional liquid chromatagraph or spectrophotometer C by way of a filter F which may remove fillers and other components of the sample unrelated to the assay, or the sample may be injected into suitable autovials for auto samples.

Using my extraction and analysis system, one obtains relative standard deviations (RSD) as low as 1% repeatedly without concern for human error. Thus, when analyzing several samples of a particular product, if the results of the assays are different, one can be assured that the error stems from production of the samples rather than from the analysis thereof.

It will thus be seen that the objects set forth, among those made apparent from the preceding description, are efficiently attained. Also, certain changes may be made in carrying out the above method and in the construction set forth without departing from the scope of the invention. For example, in some cases it may be desirable to separate the slot 34 and knife edge 34b so that they are located at different positions around chamber 28, e.g. 180° apart. In this case, relief 82 would be located just ahead of the knife edge. Also, if deemed desirable, more than one slot and/or knife edge may be provided. Therefore, it is intended that all matter contained in the above description or shown in the accompanying drawings shall be interpreted as illustrative and not in a limiting sense.

It is also to be understood that the following claims are intended to cover all of the generic and specific features of the invention herein described.

I claim:

1. A tablet extraction system comprising
    means defining a cylindrical chamber having a longitudinal axis, a cylindrical side wall and a bottom wall;
    means defining at the interior surface of the chamber side wall a relatively sharp knife edge which extends in the general direction of said axis;
    means defining in a sector of the chamber side wall adjacent to the knife edge a relief which lies radially outboard of said knife edge;
    an impeller rotatably mounted in said chamber for rotation about said axis, said impeller including a rigid finger which extends along said chamber, said finger having a generally cylindrical outer surface which conforms closely to unrelieved portions of said chamber side wall and a leading face which extends from said cylindrical surface toward said axis;
    means defining an opening in said bottom wall into said chamber;
    means defining an opening in said side wall into said chamber, and
    means for rotating said impeller so that said finger leading face is rotated toward said knife edge whereby when an extractor is probed into a liquid-containing vessel and the impeller is rotated, the impeller can recirculate the liquid and a tablet entrained in the liquid through said chamber for mixing and can position the tablet while in the chamber for impaction against the knife edge to pulverize the tablet.

2. The extraction system defined in claim 1 wherein the side opening is a slot which is located between said knife edge and said relief.

3. The extraction system defined in claim 2 wherein said knife edge and said finger are substantially co-extensive in the direction of said axis.

4. The extraction system defined in claim 1 wherein said side opening, said knife edge and said finger are substantially co-extensive in the direction of said axis.

5. The extraction system defined in claim 1 and further including a concavity in said finger leading face for cradling a tablet so that a surface of the tablet can face the knife edge when said finger rotates toward the knife edge.

6. A tablet extraction system comprising
    an impeller having a rotary axis and including a rigid finger which is spaced from and extends in the general direction of said axis, said finger having a radially outer surface and a leading face which extends from said radially outer surface toward said axis;
    means for rotating the impeller about said axis so that said finger sweeps out a toroidal envelope;
    a housing enclosing said impeller, said housing having a first wall which extends generally parallel to said axis and a second wall which extends generally perpendicular to said axis opposite said finger, said first and second walls defining a chamber which encloses said impeller;
    means defining a knife edge in said chamber, said knife edge extending generally parallel to said axis and being located only slightly radially outward from said toroidal envelope;
    means defining a first opening in the housing first wall, and
    means defining a second opening in the housing second wall.

7. The system defined in claim 6 wherein said finger leading face has a concavity.

8. The system defined in claim 6 wherein said first opening is adjacent to said knife edge.

9. The system defined in claim 8 wherein said first opening is a slot that extends generally parallel to said axis.

10. The system defined in claim 9 wherein said finger, said knife edge and said slot are substantially co-extensive in the direction of said axis.

11. The system defined in claim 6 wherein
    said knife edge is located adjacent to a selected sector of said housing first wall, and
    said selected first wall sector is spaced radially outward from said knife edge.

12. The system defined in claim 11 and further including means defining a concavity in said finger leading face.

13. The system defined in claim 11 wherein said first opening is located adjacent to said selected first wall sector.

14. The system defined in claim 13 wherein said selected first wall sector, said first opening and said knife edge are positioned angularly about said axis in that sequence in said housing.

15. The system defined in claim 14 wherein said finger, said knife edge and said first opening are substantially co-extensive in the direction of said axis.

16. The method of extracting a tablet comprising the steps of
    immersing a tablet in a liquid diluent;
    inserting into the diluent a probe having an interior cavity, bottom and side openings leading into the cavity and an impeller in the cavity which can be rotated about an axis that is aligned with the bottom opening;
    rotating the impeller about said axis to draw the diluent and tablet into the cavity through the bottom opening and to spin the tablet around said axis;
    impacting the spinning tablet against a knife edge in the cavity to break up the tablet into smaller particles which may be ejected from the cavity through the side opening;
    continuing the rotation of the impeller to recirculate the diluent and tablet particles through the cavity and impact the particles against the knife edge so that the particles are broken up into progressively smaller particles that dissolve in the recirculating diluent until the tablet is completely extracted.

17. The method defined in claim 16 and including the additional step of interrupting the rotation of the impeller at least once during the extraction.

18. The method defined in claim 16 and including the additional step of orienting the spinning tablet in the probe cavity so that the tablet is edge-on to the knife edge.

* * * * *